United States Patent
Pruett

Patent Number: 5,660,840
Date of Patent: Aug. 26, 1997

[54] FACIAL TREATMENT SYSTEM USING COSMETIC PREPARATION AND FACIAL MASK

[76] Inventor: Stephanie L. Pruett, 821 McSwain Rd., Shelby, N.C. 28150

[21] Appl. No.: 639,404

[22] Filed: Apr. 29, 1996

[51] Int. Cl.$^6$ .................................. A61K 7/48
[52] U.S. Cl. .................. 424/401; 424/402; 514/844; 514/846; 514/847
[58] Field of Search .................... 424/401, 402; 514/844, 846, 847; 132/319

[56] References Cited

U.S. PATENT DOCUMENTS

| | | | |
|---|---|---|---|
| 194,815 | 9/1877 | Emerson-French. | |
| 441,009 | 11/1890 | Jenkins | 424/401 |
| 3,806,593 | 4/1974 | Swanbeck et al. | 424/401 |
| 3,810,996 | 5/1974 | Sutliff et al. | 424/401 |
| 4,297,374 | 10/1981 | Wess | 424/401 |
| 4,690,821 | 9/1987 | Smith et al. | 424/401 |
| 4,911,925 | 3/1990 | Shatkina et al. | 424/401 |
| 4,917,891 | 4/1990 | Kaufmann et al. | 424/401 |

*Primary Examiner*—Thurman K. Page
*Assistant Examiner*—K. Shelborne

[57] ABSTRACT

A system for moisturizing the skin and decreasing established acne is presented. The system consist of a therapeutic preparation comprised of bananas, orange juice, and coconut milk. An alternative procedure consist of the use of a conventional cleanser, toner, facial scrub, and moisturizer. These preparations provide moisturizing benefits, performs a skin sloughing treatment, and alleviates many undesirable skin conditions, including acne. The preparation is used with a facial mask which seals the therapeutic skin treatment on the skin and protects the skin from bacteria and contaminants.

5 Claims, No Drawings

FACIAL TREATMENT SYSTEM USING COSMETIC PREPARATION AND FACIAL MASK

The present invention relates to the field of hygienic/ cosmetic preparation for moisturizing the skin and decreasing established acne and in some cases a prevention of acne.

BACKGROUND

During their lifetimes, most people experience undesirable skin conditions, such as acne, often beginning at pre-adolescenee. Dry skin, loss of firmness and elasticity accompanies the aging process. Women, in particular, turn to cosmetic treatments for enhancing the appearance of the skin, however, men can also benefit from this procedure.

An innovative approach to skin problem involves a process of applying banana followed by orange juice and coconut milk to the face, along with a facial mask that conforms to the face. An alternative method uses a conventional cleanser, toner, facial scrub, then a moisturizer applied generously to the face, along with a facial mask that conforms to the contour of the face.

DESCRIPTION OF THE INVENTION

In its simplest form, the natural skin treatment preparation is composed of two tablespoons banana which are first applied to the face after cleansing, and then followed by orange juice and coconut milk, which is applied to the face over the banana application using a cotton ball. A facial mask would then be applied overnight. An additional process would be to cleanse the face using a conventional cleanser and application of a toner with a cotton ball. This would then be followed by use of a facial scrub as needed, accompanied by the use of a generous amount of moisturizer. Finally, the facial mask would be applied overnight to produce the same results. A suitable preparation comprises the use of two tablespoons banana, one cubic centimeter orange juice and one cubic centimeter coconut milk.

PROCESS FOR SKIN TREATMENT

The steps of treatment are to cleanse the face with a conventional cleanser, apply conventional toner, and use facial scrub as needed. Follow this with a generous amount of conventional moisturizer. However, this procedure can be used by first cleansing the face and then applying approximately two tablespoons of fresh banana to the face. Follow this treatment by applying orange juice and coconut milk to the face using a cotton ball. Cover the face with a pliable plastic facial mask overnight. Pull off mask: cleanse face with conventional cleanser, and apply moisturizing cream or lotion. Sanitize the mask for reuse. Consequently, this can also be used by cleansing hands and feet and wearing a specially prepared bootie for feet and gloves for hands to lock in moisture.

A panel of men and women used this therapeutic skin treatment process and confirmed the benefits of using this approach.

BENEFITS FROM USING THERAPEUTIC SKIN TREATMENT

1. Improved skin tone
2. Immediately noticeable improvement in skin texture
3. Removal of excess oils
4. Skin sloughing treatment performed
5. Acne dried and healed
6. Skin moisturized
7. Aging skin rejuvenated In addition, using a facial mask with the preparation helps to keep the compound on the surface of the skin. This allows the skin to draw from a reservoir during the sleeping hours-giving the face the moisture it needs. The mask also protects skin from contaminants and bacteria in the environment which clog pores that cause acne. The mask conforms to the contour of the face, is easy to use and allows for ease of movement.

Skin care systems using masks are not a new idea as exemplified by the following patents:

U.S. Pat. No. 3,806,593, to Swanbeck, issued Apr. 23, 1974. This invention is limited to treatment of skin problems, especially acne.

U.S. Pat. No. 4,634,436, to La Tour, issued Jan. 6, 1987 provided temporary relief from affliction.

U.S. Pat. No. 2,002,449, to Dohm, issued Oct. 18, 1934 is for a dermatoid face mask used with commercial lotions, creams, astringents, etc.

U.S. Pat. No. 3,810,996 to Sutliff; issued May 14, 1974 is a cosmetic facial mask composed of an aqueous paste.

U.S. Pat. No. 5,026,552 to Gueret, issued Jun. 25, 1991 is for a cleaning compound using a mesh in which gel is confined.

U.S. Pat. No. 194,815 to Emerson, issued Sep. 4, 1877 is for a toilet mask to which certain lotions can be applied for healing or softening of the skin.

I claim:

1. A skin moisturizing therapeutic system comprising a preparation consisting of two table spoons banana, one cubic centimeter orange juice and one cubic centimeter coconut milk.

2. A skin moisturizing therapeutic system comprising of a cleanser, toner, facial scrub, two tablespoons banana, one cubic centimeter orange juice and one cubic centimeter coconut milk.

3. The system of claim 2 further comprising a pliable plastic facial mask.

4. A skin treatment process for moisturizing the face comprising the application of the preparation of claim 1 to the skin.

5. A skin treatment process for moisturizing the skin comprising the application of the system of claim 2 to the face followed by the application of a facial mask, said facial mask being applied overnight to protect the face from bacteria and contaminants.

* * * * *